(12) United States Patent
Luo et al.

(10) Patent No.: US 8,159,288 B2
(45) Date of Patent: Apr. 17, 2012

(54) LOW POWER BPSK DEMODULATOR

(75) Inventors: Zhenying Luo, Medford, MA (US);
Sameer Sonkusale, Arlington, MA (US)

(73) Assignee: Tufts University, Medford, MA (US)

( * ) Notice: Subject to any disclaimer, the term of this patent is extended or adjusted under 35 U.S.C. 154(b) by 0 days.

(21) Appl. No.: 12/528,967

(22) PCT Filed: Feb. 27, 2008

(86) PCT No.: PCT/US2008/055124
§ 371 (c)(1),
(2), (4) Date: Jun. 21, 2010

(87) PCT Pub. No.: WO2008/106512
PCT Pub. Date: Sep. 4, 2008

(65) Prior Publication Data
US 2010/0277234 A1 Nov. 4, 2010

Related U.S. Application Data

(60) Provisional application No. 60/892,041, filed on Feb. 28, 2007.

(51) Int. Cl.
*H03D 3/00* (2006.01)
*H04L 27/22* (2006.01)
*H04L 27/227* (2006.01)

(52) U.S. Cl. ........ 329/307; 329/305; 329/310; 375/324; 375/326

(58) Field of Classification Search .......... 329/304–310; 375/324–328
See application file for complete search history.

(56) References Cited

U.S. PATENT DOCUMENTS
4,491,805 A * 1/1985 Laures et al. .................. 331/18

FOREIGN PATENT DOCUMENTS
EP 0 533 208 A2 9/1992

OTHER PUBLICATIONS

Harb et al., "Low-power CMOS interface for recording and processing very low amplitude signals," J. Analog Integrated Circuits Signal Process., vol. 39, pp. 39-54, 2004.
Ghovanloo et al., "A Modular 32-site wireless neural stimulation microsystem," IEEE J. Solid-State Circuits, vol. 39, No. 12, Dec. 2004, pp. 2457-2466.

(Continued)

*Primary Examiner* — David Mis
(74) *Attorney, Agent, or Firm* — Proskauer Rose LLP

(57) ABSTRACT

A low power BPSK demodulator having a simple architecture, compact design and reliable is provided. The BPSK demodulator includes a first branch (210) having a first mixer (212) and a first low pass filter (214), a second branch (220) coupled to the first branch at the output of the first low pass filter (214) and input of the first mixer (212) and having a second mixer (222), and a third branch (230) coupled to the second branch at the input and output of the second mixer (222) and having a third mixer (232) a second low pass filter (234) and a voltage control oscillator (236), wherein the third branch and the second branch form a charge pumped based phase lock loop that locks onto a carrier frequency of the BPSK demodulator.

12 Claims, 16 Drawing Sheets

OTHER PUBLICATIONS

Liu et al., "A neuro-stimulus chip with telemetry unit for retinal prosthetic device," Solid-State Circuits, IEEE Journal of vol. 35, Issue 10, Oct. 2000, pp. 1487-1497.

Cahn, C., "Improving Frequency Acquisition of a Costas Loop", Communications, IEEE Transactions on [legacy, pre-1988], vol. 25, Issue 12, Dec. 1977, pp. 1453-1459.

Peric et al., "Improving Costas loop pull in range using pseudo BER detector" Telecommunications in Modern Satellite, Cable and Broadcasting Service, 2001. TELSIKS 2001. 5th International Conference on, vol. 2, Sep. 19-21, 2001, pp. 753-756.

Luo, Z., et al., "A Novel Low Power BPSK Demodulator," IEEE, 2007, pp. 3856-3858.

Sonkusale, S., et al., "A Wireless Data and Power Telemetry System Using Novel BPSK Demodulator for Non-Destructive Evaluation of Structures," IEEE, 2007, pp. 300-303.

International Preliminary Report on Patentability for PCT/US2008/055124, International Filing Date Feb. 27, 2008.

International Search Report for PCT/US2008/055124, International Filing Date Feb. 27, 2008.

* cited by examiner

LOW POWER BPSK DEMODULATOR

CROSS REFERENCE TO RELATED APPLICATIONS

This application is a national stage application of International Application No. PCT/US2008/55124 filed Feb. 27, 2008, which claims the benefit of and priority to U.S. Provisional Application No. 60/892,041, filed Feb. 28, 2007. The entire disclosure of these applications is incorporated herein by reference.

BACKGROUND

Biological implants, radio frequency identification device ("RFID") tags, and smart credit cards utilize low bit-rate short distance communications. Power consumption is of utmost importance in such applications. Recently there has been a lot of attention to the development of implantable electronic devices, for medical treatment and rehabilitation. In such biological implants, external data transmitters communicate control and data signals to the implant wirelessly. For example, deep brain implants are used to control seizures in epileptic patients where the external command signals may include information about pattern for micro-stimulation and feedback. At the same time the external controller is also responsible to deliver power to the implant device wirelessly. This method of power delivery is called power telemetry. Due to limited efficiency of such power delivery, it places a critical constraint on the power consumption of the embedded transceivers. In these applications, it has been found that Binary Phase Shift Keying ("BPSK") is a more suitable protocol of communication than Amplitude Shift Keying ("ASK") and Frequency Shift Keying ("FSK"). The reason for this is that BPSK has fixed signal amplitude and a constant carrier frequency. Constant amplitude carrier signal provides a stable power transfer at high transfer efficiency and the constant carrier frequency allows the use of fixed sized antennas designed for optimal data and power coupling. BPSK transceivers have been designed for biological implants with great success.

FIG. 1A shows a block diagram of a squaring loop design type BPSK demodulator 100. The squaring loop design 100 is one of the earliest circuits used for the detection of BPSK signals. The squaring loop design 100 includes a square device 110, a divide-by-2 frequency divider 120, and a phase lock loop ("PLL") 130. The PLL includes a low pass filter ("LPF") 132 and a voltage control oscillator ("VCO") 134. The squaring loop design 100 extracts a carrier signal 140 by using the square device 110 to cancel the data riding on top of it, but in the process the square device 110 doubles the carrier frequency. Therefore, the divide-by-2 frequency divider 120 is needed to extract the carrier frequency once the phase lock loop (PLL) 130 locks onto the doubled carrier frequency.

FIG. 1B shows a block diagram of a BPSK demodulator using a Costas loop design 150. The Costas loop design is a very successful solution for coherent detection of BPSK signals. The Costas loop design includes a lower branch 160, an upper branch 170, and a center branch 180. The upper and lower branches 160, 170 include respective mixers 162, 172 and LPFs 164, 174. The center branch 180 includes a mixer 182, a LPF 184, a VCO 184, and a quadrature signal generator 188. The quadrature signal generator 188 generates two signals with identical frequency, but each signal has a 90 degree phase difference. These two signals are independently multiplied by the BPSK signal to perform down-conversion multiplications into an "I" signal and a "Q" signal. When locked, the lower branch 160 (Q branch) together with center branch 180 form a loop that acts as a normal PLL that locks onto the carrier frequency. The BPSK data information 190 is then extracted in the upper branch 170 (I branch).

SUMMARY

Neither of the aforementioned designs is suitable for low power biological implant applications for the following reasons. The squaring devices 110 of the squaring loop design 100 are inaccurate and hard to implement using analog circuitry and thus require a digital signal processor ("DSP"). The Costas loop design 150 uses a multiplier or XOR type of Phase Detectors ("PD") that have limited acquisition and tracking range, and typically require an extra acquisition-aid circuit. Further, the quadrature signal generator 188 of the Costas Loop design 150 needs additional power requirements to produce I/Q signals as well as maintaining their relative phase offset over a range of frequencies.

In one aspect, a low power BPSK demodulator has a simple architecture that is a compact design and reliable. The BPSK demodulator includes first branch, a second branch, and a third branch. The first branch includes a first mixer and a first low pass filter. The second branch is coupled to the first branch and includes a second mixer. The third branch is coupled to the second branch and includes a second low pass filter and a voltage control oscillator. The third branch and the second branch form a charge pumped based phase lock loop that locks onto a carrier frequency of the BPSK demodulator.

In another aspect, a low power BPSK demodulator has a simple architecture that is a compact design and reliable. The low power BPSK demodulator includes a means for mixing a BPSK signal and a carrier signal to form a mixed signal. The low power BPSK demodulator further includes a means for filtering the mixed signal to form a data signal and a means for mixing the data signal and the carrier signal to form a regenerated BPSK signal. The low power BPSK demodulator further includes a means for filtering the regenerated BPSK signal to form a filtered signal and a means for oscillating the filtered signal to form the carrier signal.

In another aspect, a low power BPSK demodulation includes a method. The method includes mixing, by a first mixer, a BPSK signal and a carrier signal to form a mixed signal. The method further includes filtering, by a first low pass filter, the mixed signal to form a data signal and mixing, by a second mixer, the data signal and the carrier signal to form a regenerated BPSK signal. The method further includes filtering, by a second low pass filter, the regenerated BPSK signal to form a filtered signal and oscillating, by a voltage control oscillator, the filtered signal to form the carrier signal.

In other examples, any of the aspects above can include one or more of the following features. The third branch includes a phase frequency detector and a charge pump. The first branch includes a trigger and hold circuit for extracting data transition information from the phase lock loop fluctuation. The voltage control oscillator is a low power voltage control oscillator.

In some examples, the trigger and hold circuit includes a trigger circuit, a transistor coupled to the trigger circuit, a capacitor coupled to the transistor, a resistor coupled to the capacitor, and a D-Latch coupled to the resistor.

In other examples, the transistor is a MOSFET type transistor. BPSK data signal/information is extracted from the trigger and hold circuit.

In some examples, the trigger and hold circuit includes a counter, an RS-latch coupled to the counter, an AND gate coupled to the RS-latch, a D-latch coupled to the AND gate, and a glitch generator coupled to the AND gate.

In other examples, at each BPSK data transition, the RS-latch is triggered disabling the D-latch and enabling a counter to start counting a CARRIER signal. The D-latch is enabled and the counter is disabled when the count of the CARRIER signal equals eight.

The approaches and/or examples described herein can provide one or more of the following advantages. The embodiments provide the advantages of low power consumption, simple architecture, compact design and reliable performance.

Other aspects and advantages of the present invention will become apparent from the following detailed description, taken in conjunction with the accompanying drawings, illustrating the principles of the invention by way of example only.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 11A shows a step error response for a 3rd order PLL;

FIG. 17 shows an embodiment of a Phase Frequency Detector ("PFD").

FIG. 18 shows an embodiment of a Ring Voltage Control Oscillator ("VCO").

FIG. 19 shows an embodiment of an Inductance-Capacitance ("LC") VCO.

DETAILED DESCRIPTION

Figures 2A, 2B:
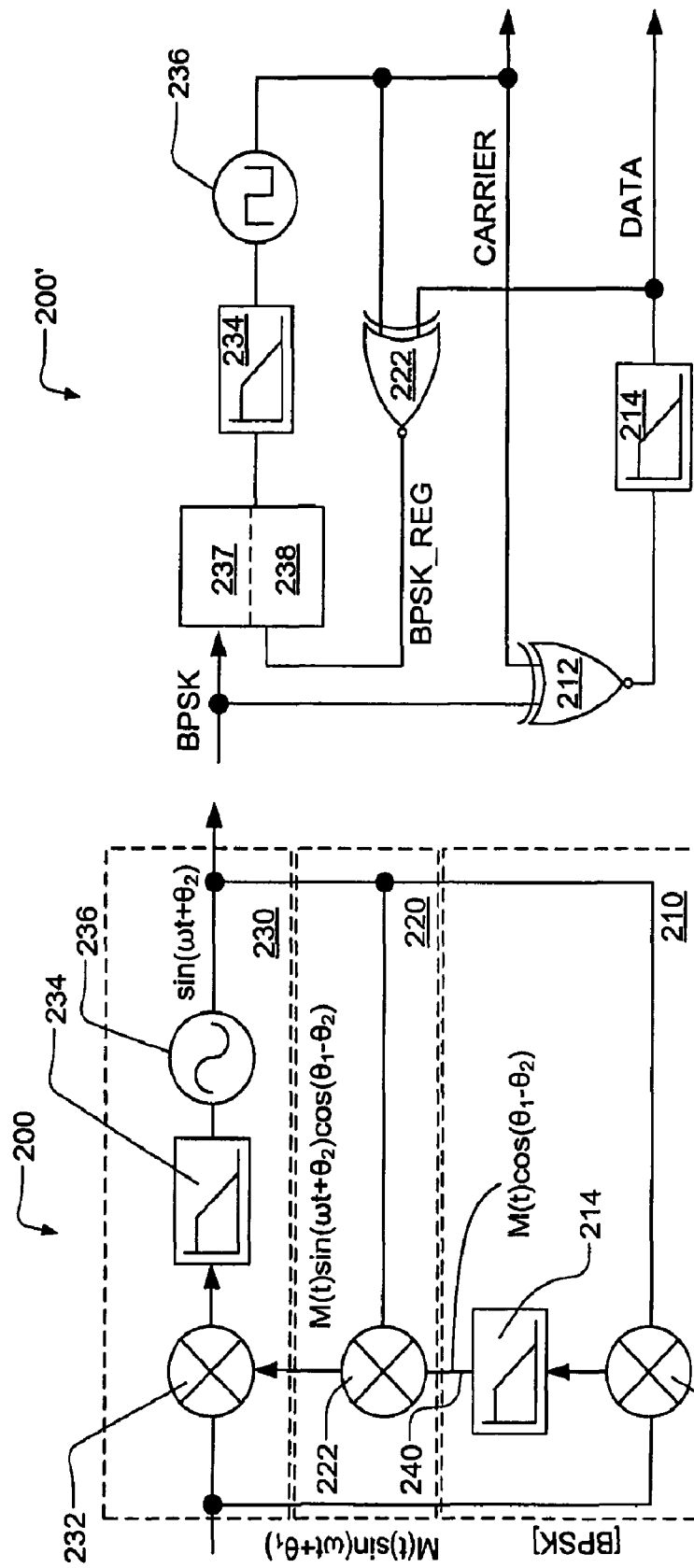
FIG. 2A shows a block diagram of one embodiment of a low power BPSK demodulator.
FIG. 2B shows a simple circuit implementation of the BPSK demodulator of FIG. 2A.

FIG. 2A shows a block diagram of one embodiment of a BPSK demodulator 200. The BPSK demodulator 200 includes a lower branch 210, an upper branch 230, and a center branch 220. The lower branch 210 includes a mixer 212 and a LPF 214; the center branch includes a mixer 222; and the upper branch includes a mixer 232, a LPF 234, and a VCO 236. When locked, the upper branch 230 together with center branch 220 form a charge pump based loop that acts as a normal PLL that locks onto the carrier frequency.

The BPSK data signal (M(t)) is either "1" or "−1". Once the loop is locked, the phase difference between $\theta 1$ and $\theta 2$ becomes zero. The VCO 236 generates exactly the carrier signal. The mixer 212 mixes the BPSK and the carrier signals, leaving only the data signal (M(t)) after the LPF 214 ($\cos(\theta 1-\theta 2)=1$ when $\theta 1=\theta 2$). The mixer 222 regenerates the BPSK signal by multiplying the carrier signal from the VCO 236 and the data signal from LPF 214. The loop continuously locks if the incoming BPSK and regenerating BPSK signals are identical. The BPSK data information 240 is extracted after LPF 214. The BPSK demodulator 200 provides the following advantages: 1) all components are simple circuit blocks; 2) no squaring component or quadrature signal generator are required; and/or 3) no complicated digital signal processing elements are required.

FIG. 2B shows a simple circuit 200' implementation of the BPSK demodulator 200 of FIG. 2A including a Phase Frequency Detector ("PFD") 237 and a Charge Pump ("CP") 238 used in the upper loop 230. The PFD 237 and CP 238 provide a more robust architecture in terms of frequency acquisition and tracking performance. When locked, the upper branch 230 together with the center branch 220 form a loop that acts as a normal PLL that locks onto the carrier frequency and the VCO 236 generates the BPSK carrier signal. The mixers 212, 222 are simply XNOR gates. The BPSK data signal/information 240 is extracted after LPF 214. However, this simple design is impractical because it relies on the ideal behavior of its components. For example, the mixers 212, 222 and the LPF 214 create a delay that causes the PLL to lose its lock for a short time during each BPSK data transition. This in turn, creates a large fluctuation in the loop that corrupts the demodulation process and destroys the stability of the loop.

Figure 3:
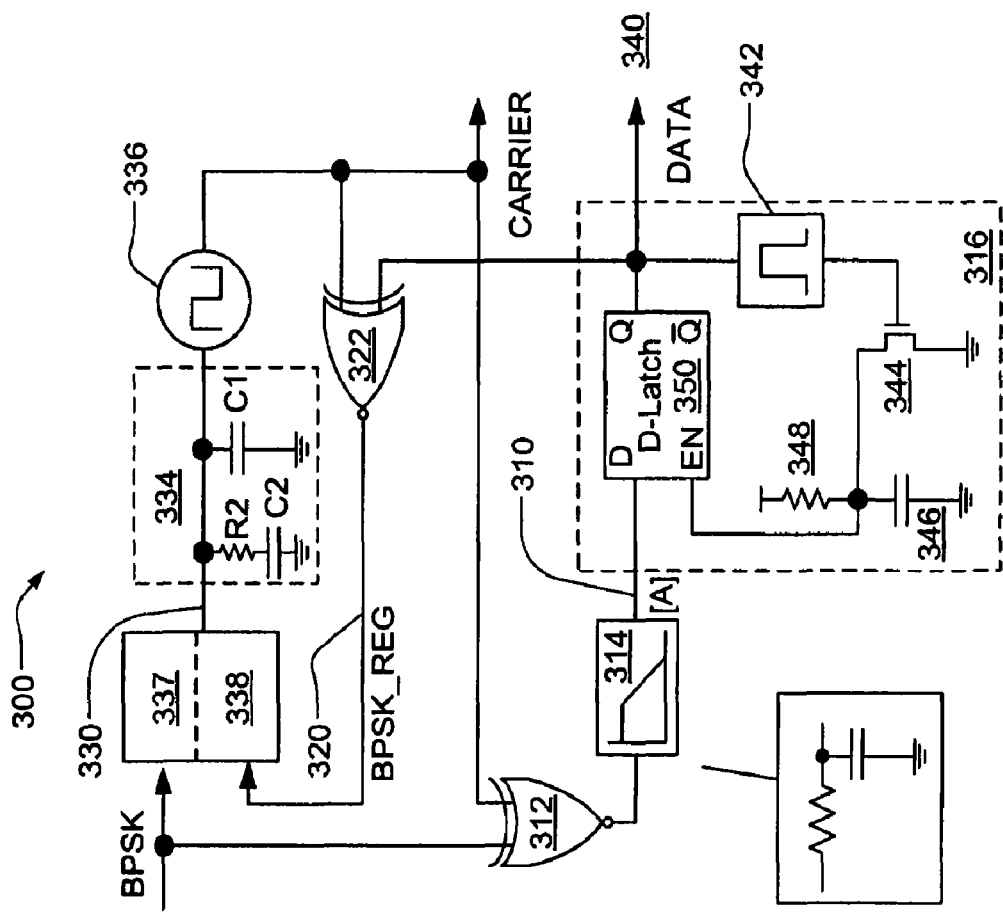
FIG. 3 shows another embodiment of a low power BPSK demodulator.

FIG. 3 shows another embodiment of a BPSK demodulator 300. The BPSK demodulator 300 includes a lower branch 310, a center branch 320, and an upper branch 330. The lower branch 310 includes a mixer 312, a LPF 314, and a trigger and hold circuit 316; the center branch 320 includes a mixer 322; and the upper branch 330 includes a LPF 334, a VCO 336, a PFD 337 and a CP 338. When locked, the upper branch 330 together with the center branch 320 form a loop that acts as a normal PLL that locks onto the carrier frequency and the VCO 336 generates the BPSK carrier signal. The mixers 312, 322 are simply XNOR gates. In one embodiment, the LPF 314 is an off-chip 1st order RC low pass filter that filters out the noisy spikes at the carrier frequency and reveals the low frequency BPSK data information at node [A]. The trigger and hold circuit 316 is used to extract the data transition information from the residual PLL fluctuation at node [A]. The BPSK data signal/information 340 is extracted from the trigger and hold circuit 316.

The trigger and hold circuit 316 includes a trigger circuit 342, a MOSFET 344, a capacitor 346, a resistor 348, and a D-Latch 350. In some embodiments, the MOSFET 344 is a n-type MOSFET. For each data transition, the MOSFET 344 is triggered to discharge the capacitor 346 and disable the D-Latch 350. The trigger and hold circuit 316 holds the data for a small duration, which is defined by the RC time constant of resistor 348 and the capacitor 346, until the PLL settles (locked) again. The D-Latch 350 has a Schmitt trigger input, which provides further noise immunity to the trigger and hold circuit 316. In one embodiment, the BPSK demodulator 300 is implemented in an AMI 0.5 μm CMOS process.

Figure 4:
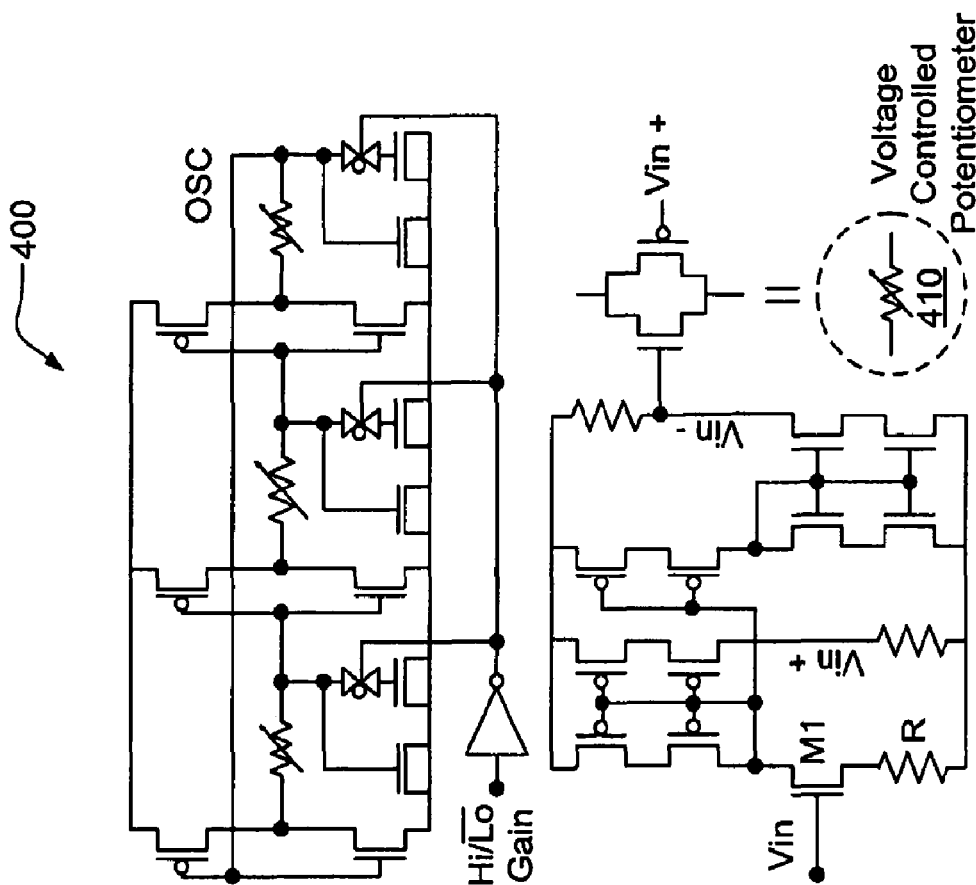
FIG. 4 shows one embodiment of a schematic diagram of an embodiment of a voltage control oscillator.

FIG. 4 shows one embodiment of a schematic diagram of a voltage control oscillator ("VCO") 400 used in the above described embodiments. In one embodiment, the VCO 400 is a simple 3-stage ring oscillator used over a wide frequency range. Vin is converted into Vin+ and Vin− to control the impedance of three potentiometers 410, which are transmission gates realized with p and n MOSFET pairs. Together with dummy transistor capacitors, these potentiometers 410 provide a tunable RC delay, and thus a tunable oscillation frequency. Three transmission gates turn on or off another three dummy transistor capacitors to provide high/low gain mode options. In this way, it is more flexible to select the desired VCO gain and center oscillation frequency when the large process variations are considered. It should be understood that other embodiments are available.

Figures 1A, 1B:
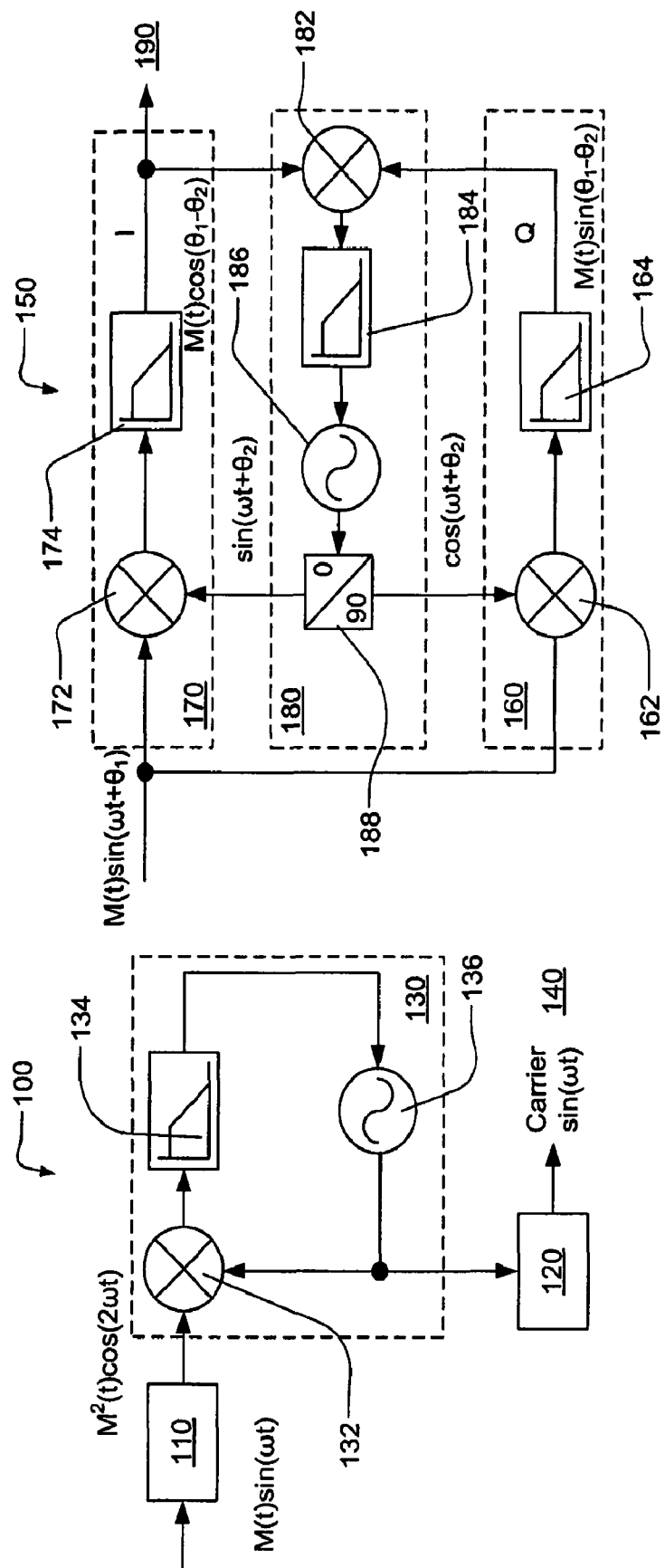
FIG. 1A shows a block diagram of a squaring loop design type BPSK demodulator.
FIG. 1B shows a block diagram of a BPSK demodulator using a Costas loop design.
Figure 5:
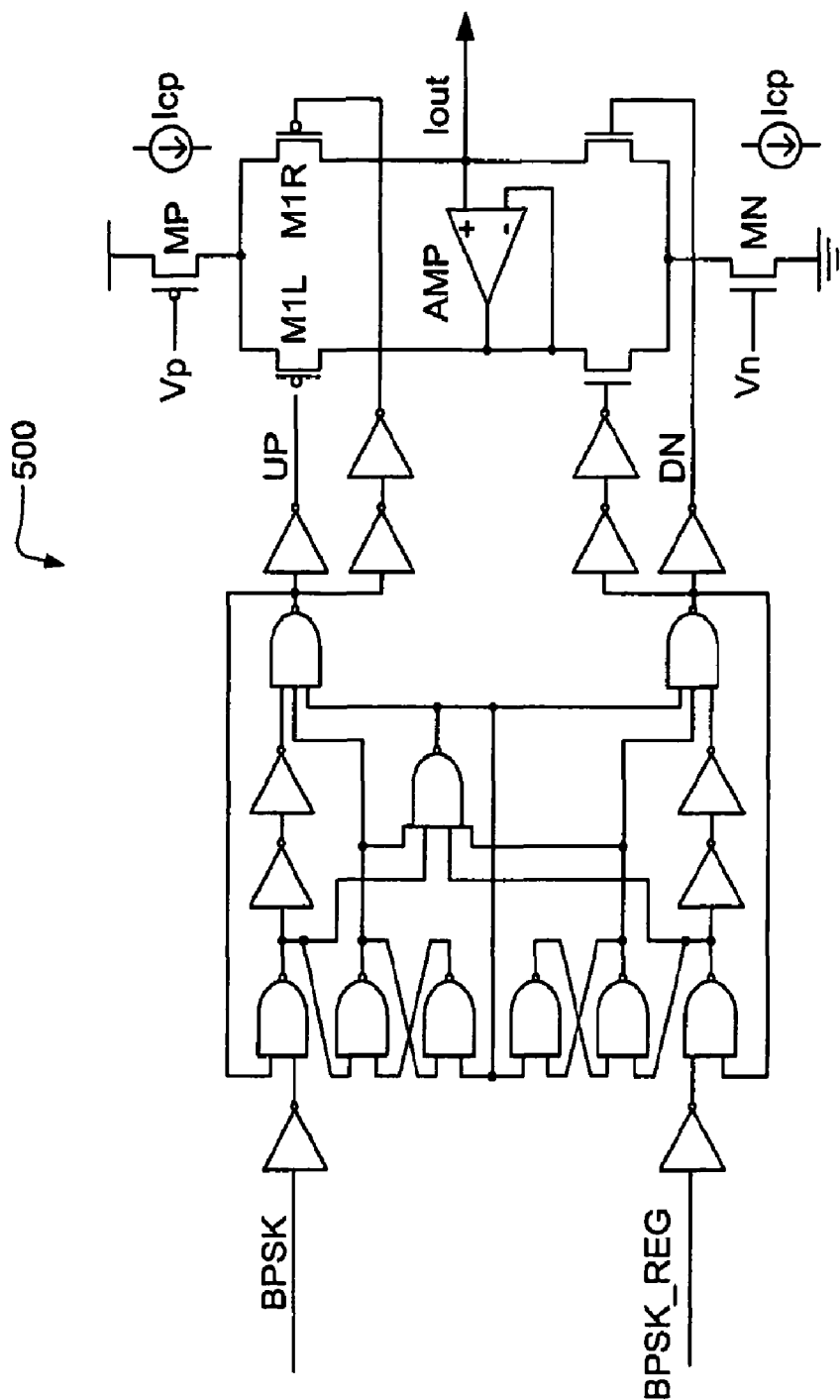
FIG. 5 shows one embodiment of a schematic diagram of a combined Phase Frequency Detector and Charge Pump.

FIG. 5 shows one embodiment of a schematic diagram of a combined PFD and CP 500 used in the above described embodiments. The combined PFD and CP 500 provides a better phase locking performance than a multiplier or XOR type phase detector would in the Costas loop design as described in FIG. 1B. Referring to FIG. 5, when MOSFETs M1R and M2R are off, MOSFETs M1L and M2L steer the current ("Icp") from the output and keep the two current sources functioning properly allowing for better control of the Icp once it is connected to the output. An amplifier ("AMP") is connected as a follower and keeps the voltage across each of the current sources stable and reduces the static phase error introduced by the shared charge injection. It should be understood that other embodiments are available.

For example, another embodiment of a PFD is illustrated in FIG. 17. Other examples are well known in the art as illustrated in William F. Egan, "Phase-Lock Basics", Wiley-Interscience, which is hereby incorporated by reference.

Figure 6:
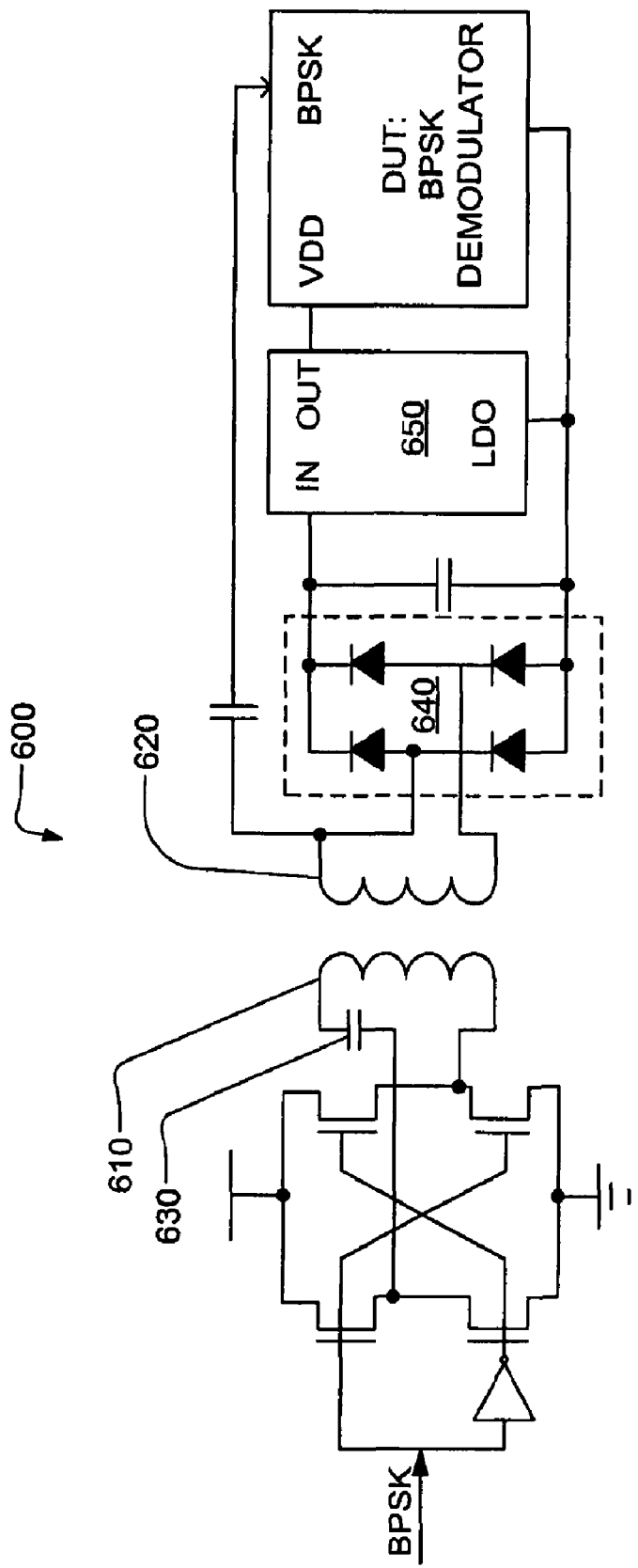
FIG. 6 illustrates a system for testing the BPSK demodulator of FIG. 3.
Figure 7:
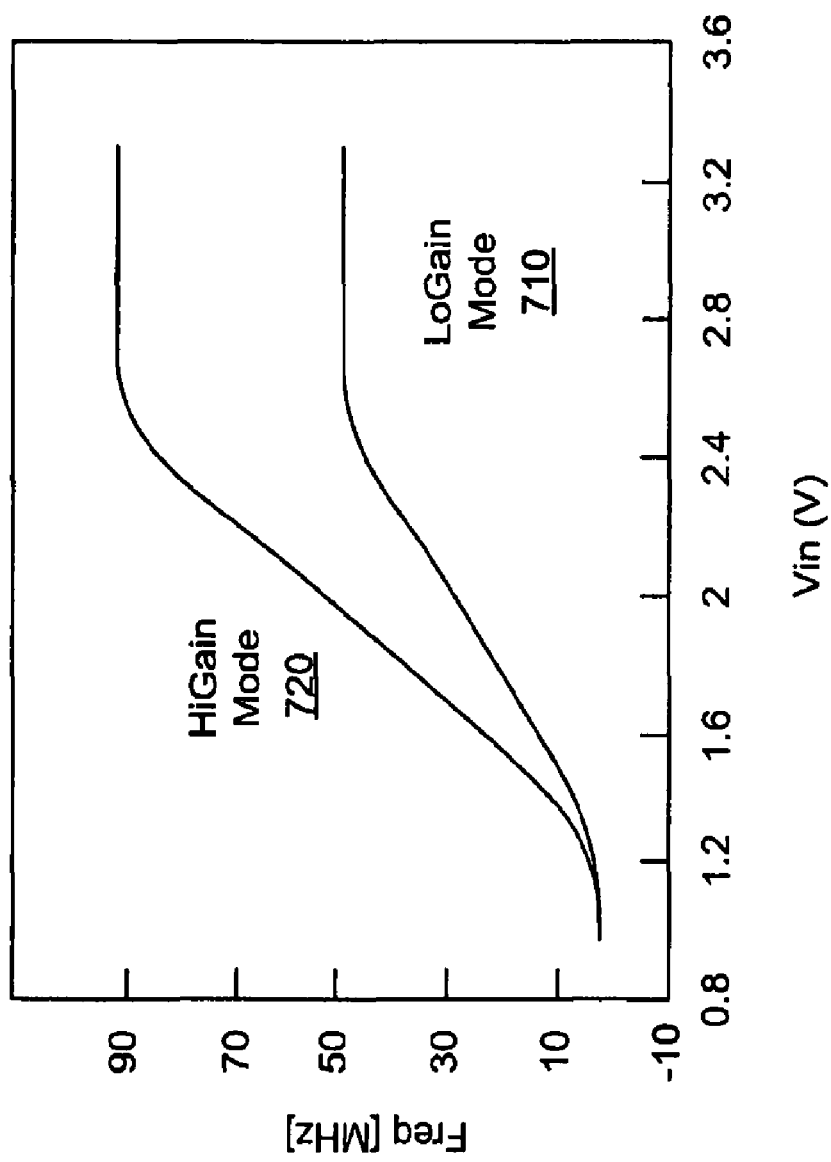
FIG. 7 shows one embodiment of a tuning range of the voltage control oscillator of FIG. 3 and FIG. 4.
Figure 8:
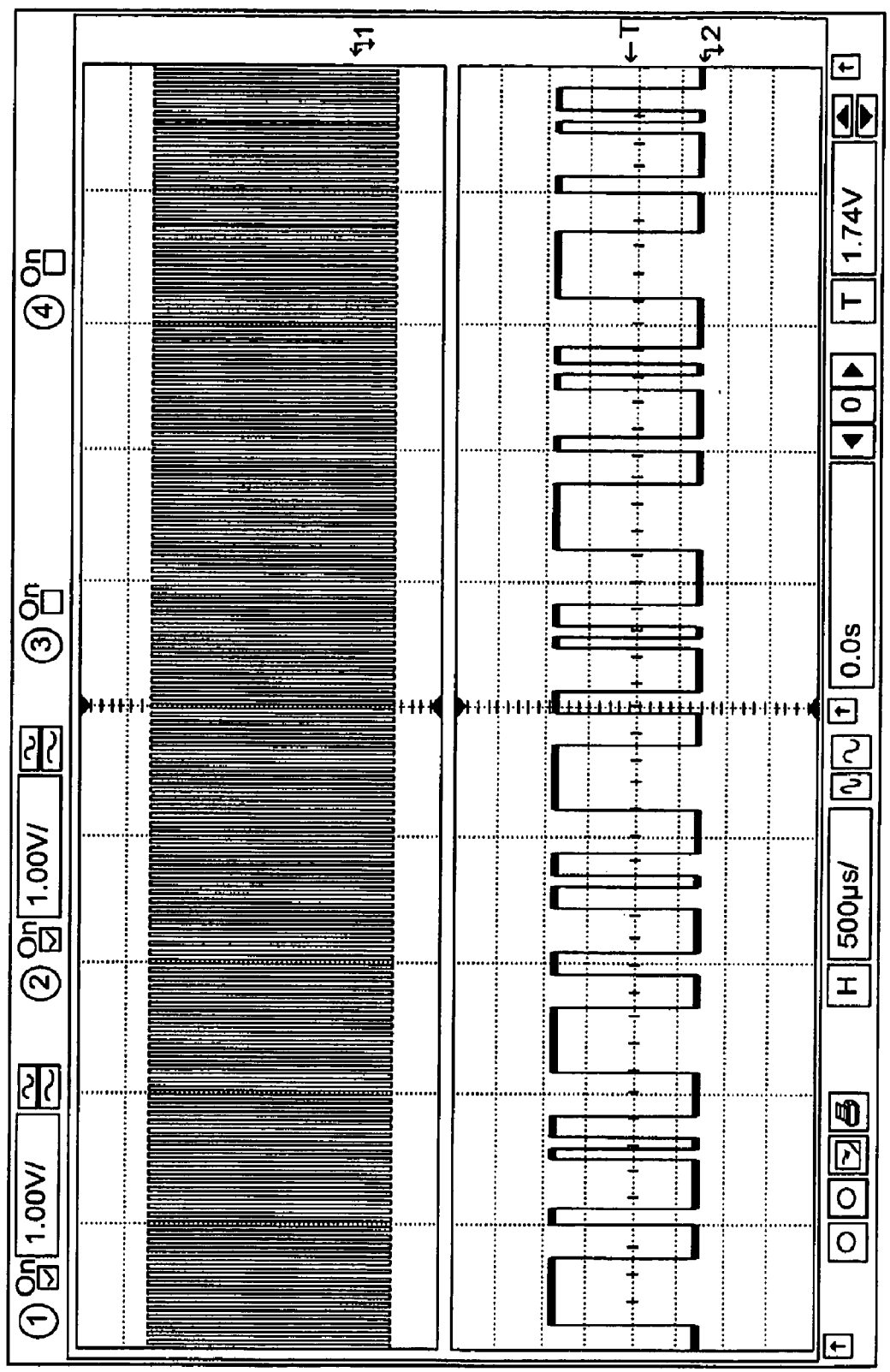
FIG. 8 shows the input BPSK signal captured at one of terminals of the second inductor of FIG. 6 and the demodulated BPSK data signal.
Figure 9:
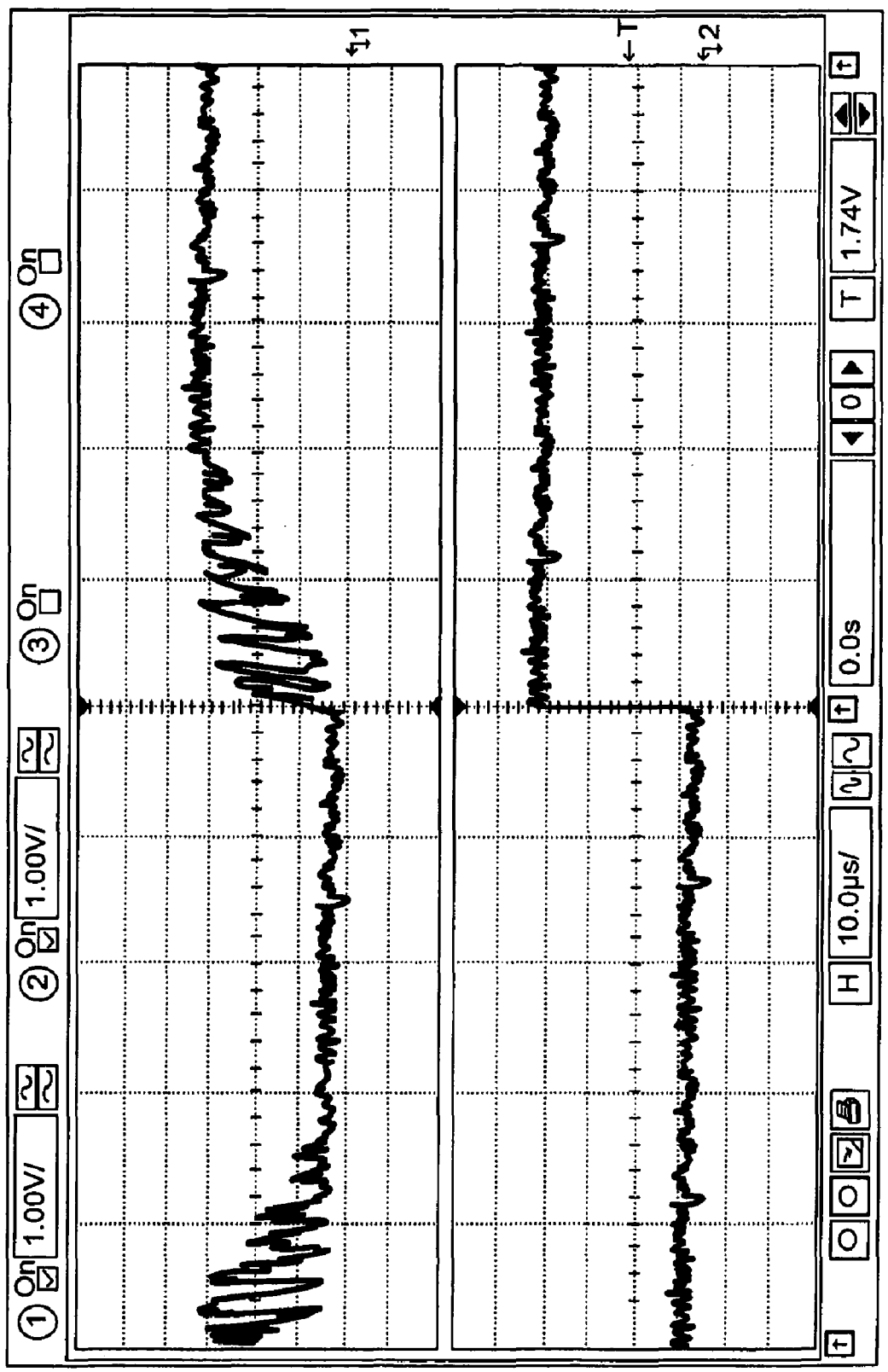
FIG. 9 shows the various waveforms of FIG. 3.

FIG. 6 illustrates a system 600 for testing the BPSK demodulator 300 as described in FIG. 3. In one embodiment, a first inductor 610 and second inductor 620 are wire coils with a diameter of 30 mm. A capacitor 630 and the first inductor 610 are tuned to resonant at the BPSK carrier frequency. By inductively coupling, power is transferred to the second inductor 620 and is further regulated by a diode bridge 640 and a low drop out regulator 650 ("LDO"). The BPSK signal is extracted at one of terminals of the second inductor 620. FIG. 7-9 illustrate the tests of the components of the BPSK demodulator 300.

FIG. 7 shows one embodiment of a tuning range of the voltage control oscillator ("VCO") 336 (FIG. 3). In the low gain mode 710, the VCO can be tuned from several hundred hertz ("Hz") to 48 megahertz ("MHz") with a gain of 43 MHz/V. In the high gain mode 720, the VCO has a maximum output frequency of 90 MHz and a gain of 78 MHz/V. It should be understood that other embodiments are available.

For example, other embodiments of a VCO include a ring VCO as illustrated in FIG. 18 and/or a LC VCO as illustrated in FIG. 19. Other examples are well known in the art as illustrated in Behzad Razavi, "Design of Analog CMOS Integrated Circuits", McGraw-Hill Science, which is hereby incorporated by reference.

FIG. 8 shows the input BPSK signal 810 captured at one of terminals of the second inductor 620 (FIG. 6) and the demodulated BPSK data signal 820. The BPSK signal 810 has a carrier signal of 13.5 MHz. The demodulated BPSK data signal 820 repeats a pattern of "1010001111001000" with a bit rate of 20 k bit/s.

FIG. 9 shows the waveforms of FIG. 3 at nodes [A] and the DATA signal 920. The waveform at nodes [A] is shown at 910 and the waveform for the BPSK data signal is shown at 920. The trigger and hold circuit 316 extracts the data transition information from the large fluctuation at node [A] and provides enough settling time to the PLL. The performance of the design is overviewed in Table I.

TABLE I

| CHIP PERFORMANCE | |
|---|---|
| Design Process | 0.5 μm CMOS |
| Carrier Frequency | 13.56 MHz |
| Supply Voltage | 3.3 V |
| Current Consumption | 910 μA |
| VCO Current | 650 μA |

Figure 10B:
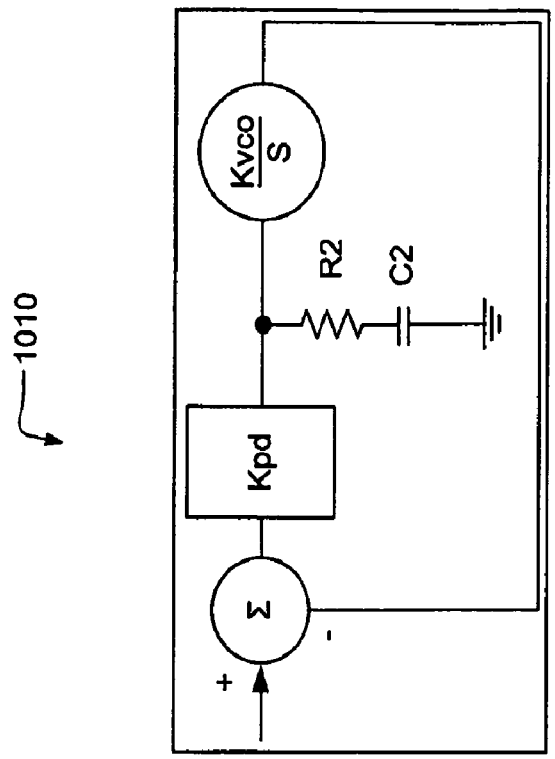
FIG. 10B shows a simplified passive loop filter configuration for analyzing a 2nd order PLL.
Figure 10A:
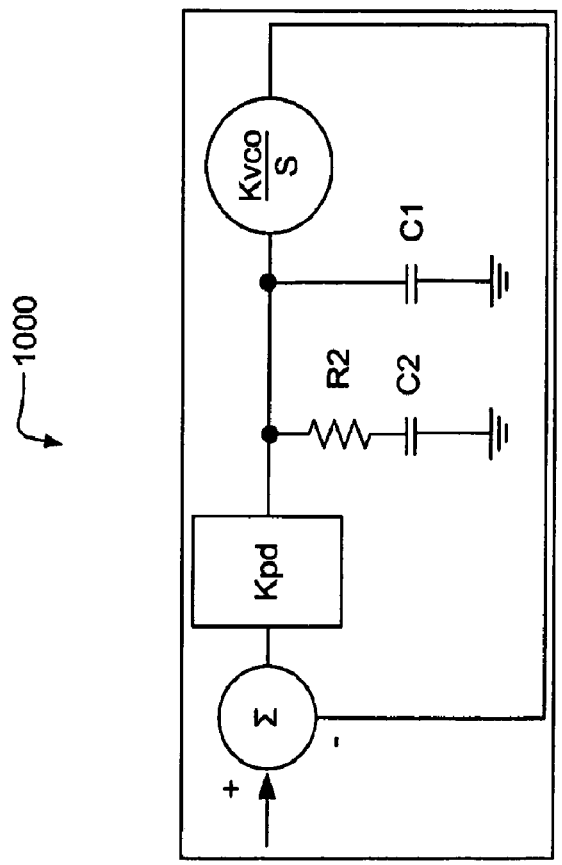
FIG. 10A shows a standard passive loop filter configuration for analyzing a 3rd order PLL.

FIG. 10A shows a standard passive loop filter configuration 1000 for analyzing a 3rd order PLL for determining the maximum data rate of the BPSK demodulator 300 (FIG. 3). The open loop gain bandwidth ("ωp") and phase margin ("Φp") are used to determine the filter component values. The open loop response is illustrated in FIG. 11A. The loop stability can be ensured by locating the point of minimum phase shift at the unity gain frequency of the open loop response. The phase margin ("Φp") is defined as the difference between 180° and the phase of the open loop transfer function at the unity gain frequency ("ωp"). The phase margin is typically chosen between 30° and 70°. In one embodiment, a 45° phase margin is selected. The loop filter component values can be calculated using the equations (1)-(3).

$$C_1 = \frac{K_\Phi K_{VCO}\tau_1}{\omega_p^2 \tau_2} \cdot \left|\frac{1+j\omega_p\tau_2}{1+j\omega_p\tau_1}\right| = 0.414 \frac{K_\Phi K_{VCO}}{\omega_p^2} \quad (1)$$

$$C_2 = C_1\left(\frac{\tau_2}{\tau_1} - 1\right) = 2\frac{K_\Phi K_{VCO}}{\omega_p^2} \quad (2)$$

$$R_2 = \frac{\tau_2}{C_2} = 1.207\omega_p \quad (3)$$

KΦ and KVCO are the transfer functions of PFD and VCO respectively.
The two time constants τ1 and τ2 are:

$$\tau_1 = R_2 \frac{C_1 C_2}{C_1 + C_2} = \tan\left(45° - \frac{\phi_p}{2}\right)/\omega_p = 0.414/\omega_p \quad (4)$$

$$\tau_2 = C_2 R_2 = 1/\omega_p^2 \tau_1 = 2.414/\omega_p \quad (5)$$

C1 removes the ripple due to the voltage drop on R2. However, if C1 is only about ⅕ to 1/10 of C2, it has a very small effect on the performance of the PLL. For Φp=45°, according to equations (1) and (2), we have C1=C2/4.83=C2/5. This allows us to ignore C1 for the following analysis, which results in the simplified passive loop filter configuration 1010 for analyzing a 2nd order PLL shown in FIG. 10B. This PLL has the frequency domain transfer function and error transfer function shown below:

$$H_{close}(s) = \omega_n^2 \frac{1 + 2\xi s / \omega_n}{s^2 + 2\xi\omega_n s + \omega_n^2} \quad (6)$$

$$H_{error}(s) = 1 - H_{close}(s) = \frac{s^2}{s^2 + 2\xi\omega_n s + \omega_n^2} \quad (7)$$

$\omega n$ and $\xi$ are the normalized bandwidth and damping factor respectively:

$$\omega_n = \sqrt{\frac{K_\Phi \cdot K_{VCO}}{C_2}} \quad (8)$$

$$\xi = \frac{R_2}{2}\sqrt{K_\Phi \cdot K_{VCO} \cdot C_2} \quad (9)$$

Substituting equations (2) and (3) into equations (8) and (9):

$$\omega n = 0.707 \, \omega p \text{ and } \xi = 0.854 \quad (10)$$

For $\xi < 1$, the step error response of the PLL in the time domain is:

$$Y_{error} = \exp(-\xi\omega_n t) \times \left[\cos(\omega_n t\sqrt{1-\xi^2}) - \frac{\xi}{\sqrt{1-\xi^2}}\sin(\omega_n t\sqrt{1-\xi^2})\right] \quad (11)$$

Figure 11B:
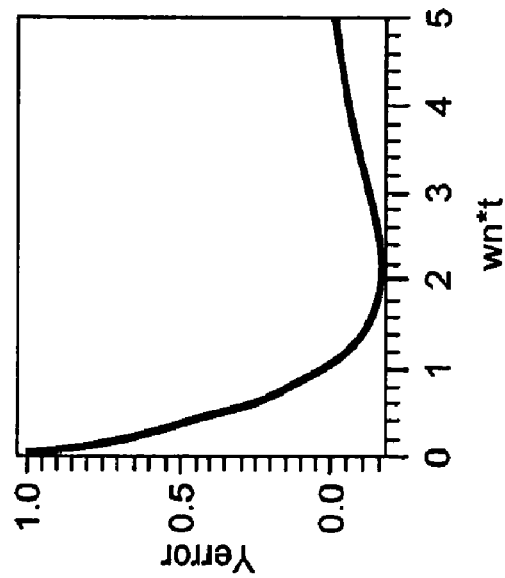
FIG. 11A shows an open loop response for a 3rd order PLL.
Figure 11A:
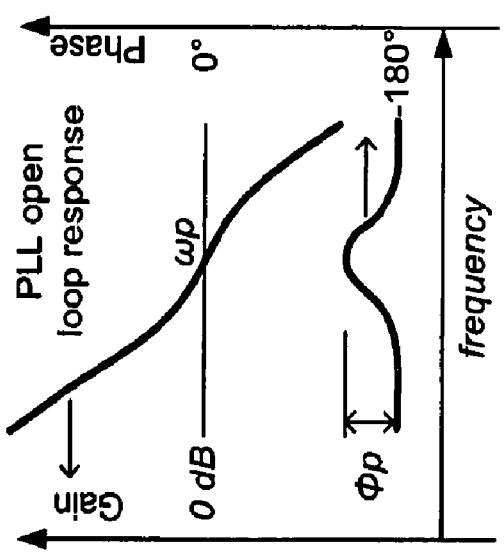

FIG. 11B shows a plot of the step error response from equation (11). When $\omega nt > 3.5$, |Yerror|<0.1, which means the PLL is almost settled. From equation (10), $\omega n$ is replaced by $\omega p$, and $t > 4.95/\omega p$, or $1/t < 0.202\omega p$. For each BPSK data transition, enough time must be provided to allow the PLL to settle (locked) before the next data transition. To satisfy this requirement, duration of each bit should be longer than $4.95/\omega p$, and the bit rate should be smaller than $0.202\omega p$. This leads to the maximum BPSK data rate of:

$$BR_{MAX} = 0.202\omega_p \quad (12)$$

$$\text{or simply } BR_{MAX} = 0.2\omega_p \quad (13)$$

The minimum hold time TH is:

$$T_H = t > 1/0.202\omega_p \approx 5/\omega_p \quad (14)$$

In order to hold the continuous time approximation, the loop bandwidth should be small relative to the carrier frequency. Otherwise, the theoretical predictions of the PLL begin to differ from the actual results, and the PLL can become unstable. Choosing the loop bandwidth to be 1/10 of the BPSK carrier frequency is enough to avoid instability:

$$\omega_p = 2\pi f_{carrier}/10 \quad (15)$$

Thus, the maximum data rate ($BR_{MAX}$) and hold time ($T_H$), in equation form, are:

$$BR_{max} = 0.202\omega_p = f_{carrier}/8 \quad (16)$$

$$T_y = 5/(2\pi f_{carrier}/10) \approx 8/f_{carrier}, \text{ or } T_H = 8 \cdot T_{carrier} \quad (17)$$

where Tcarrier is the period of the BPSK carrier signal.

In one embodiment, half of the above maximum data rate, or BR=fcarrier/16, is used as the actual upper limit of the data rate, which allows for a more robust performance.

Figure 12:
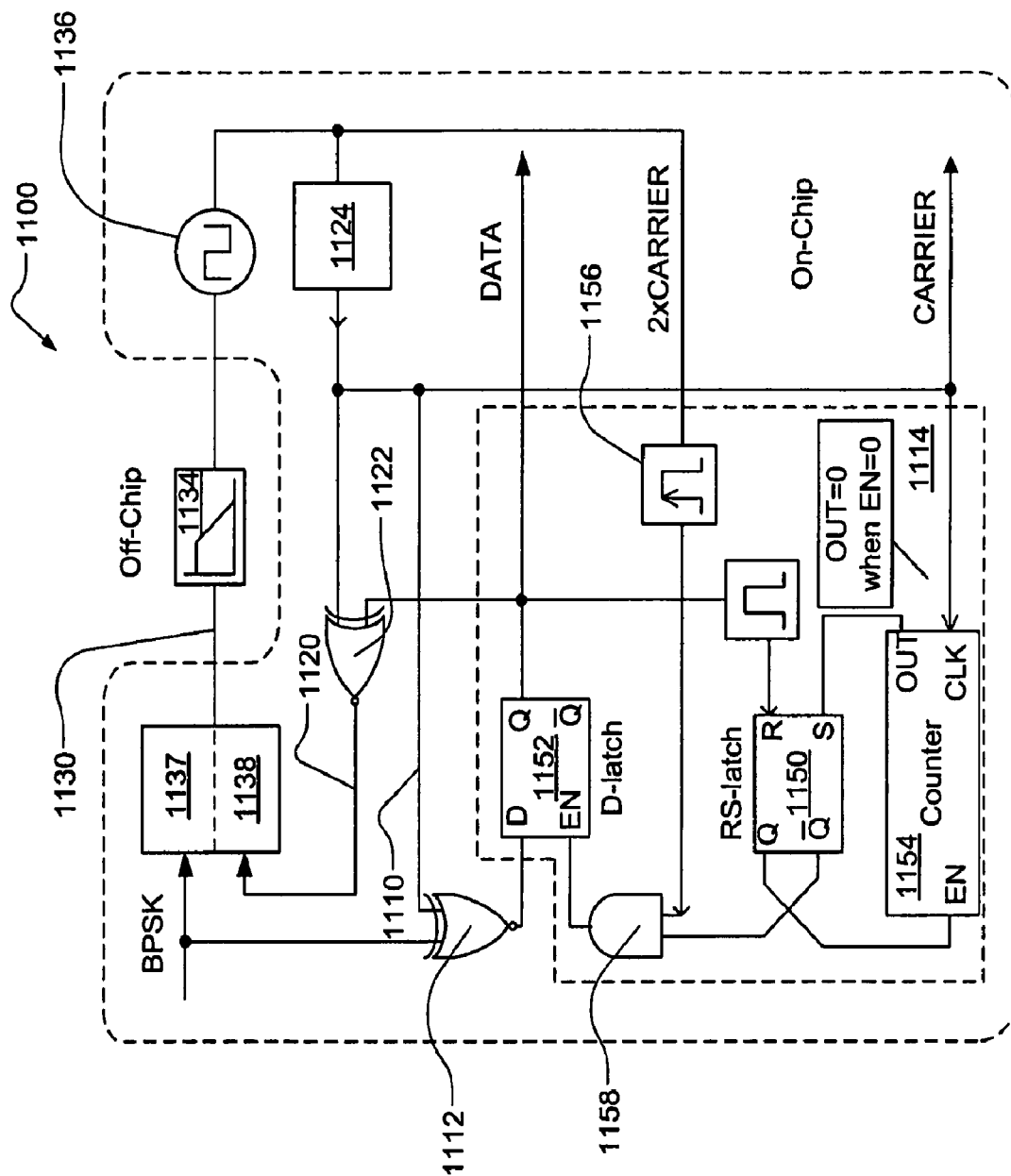
FIG. 12 shows another embodiment of a low power BPSK demodulator.

FIG. 12 shows another embodiment of a BPSK demodulator 1100. The BPSK demodulator 1100 includes a lower branch 1110, a center branch 1120, and an upper branch 1130. The lower branch 1110 includes a mixer 1112 and a trigger and hold circuit 1114; the center branch 1120 includes a mixer 1122 and a frequency divider circuit 1124; and the upper branch 1130 includes a low pass filter ("LPF") 1134, a voltage control oscillator ("VCO") 1136, a Phase Frequency Detector ("PFD") 1137 and a Charge Pump ("CP") 1138. When locked, the upper branch 1130 together with the center branch 1120 form a loop that acts as a normal PLL that locks onto the carrier frequency and the VCO 1136 generates the BPSK carrier signal.

The trigger and hold circuit 1114 includes an RS-latch 1150, a D-latch 1152, a counter 1154, a glitch generator 1156, and an AND gate 1158. At each BPSK data transition, the RS-latch 1150 is triggered at its R input, its output $\overline{Q}$ becomes low disabling the D-latch 1152 immediately. At the same time, a counter 1154 is enabled and starts counting the CARRIER signal. Once it counts to 8, it outputs "high" and flips over the RS-latch 1150. As a result, the D-latch 1152 is enabled and the counter 1154 is disabled and its output becomes low again.

Figure 13:
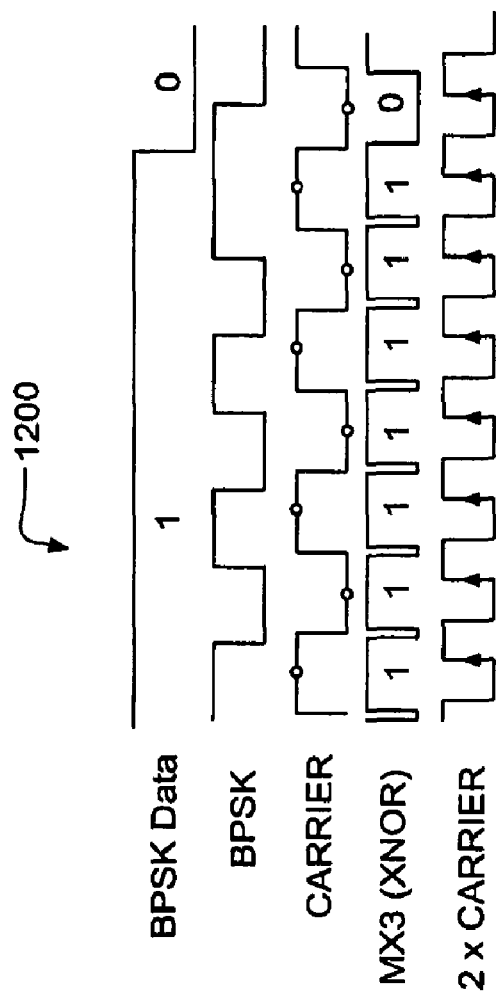
FIG. 13 shows a timing diagram of BPSK demodulator of FIG. 12.

FIG. 13 is a timing diagram 1200 of BPSK demodulator 1100 of FIG. 12. In order to extract the low frequency BPSK data signal from the mixer's 1112 output without using a LPF, the mixer's 1112 output signal is examined. Although the high frequency spikes are unavoidable, the demodulated BPSK data information is always positioned on mixer's 1112 output at the center of each half CARRIER cycle. Thus, by doubling the CARRIER frequency, the data information can be chosen on the mixer's 1112 output at each rising edge of the 2× CARRIER signal.

Using the passive loop filter configuration of FIG. 10A, the VCO 1136 generates two times the BPSK carrier frequency signal (2× CARRIER). The rising edge triggered glitch generator 1156 turns on the AND gate 1158 for a very shot time and passes only the useful demodulated data information to the DATA output. Doubling the VCO 1136 frequency slightly increases its power consumption, but the bulky off-chip RC components can be removed and the circuit becomes easier to use. Another benefit of frequency doubling is that the duty cycle of the CARRIER signal can be shaped exactly to 50% by the frequency divider 1124, which relaxes the VCO 1136 design requirement.

Figure 14:
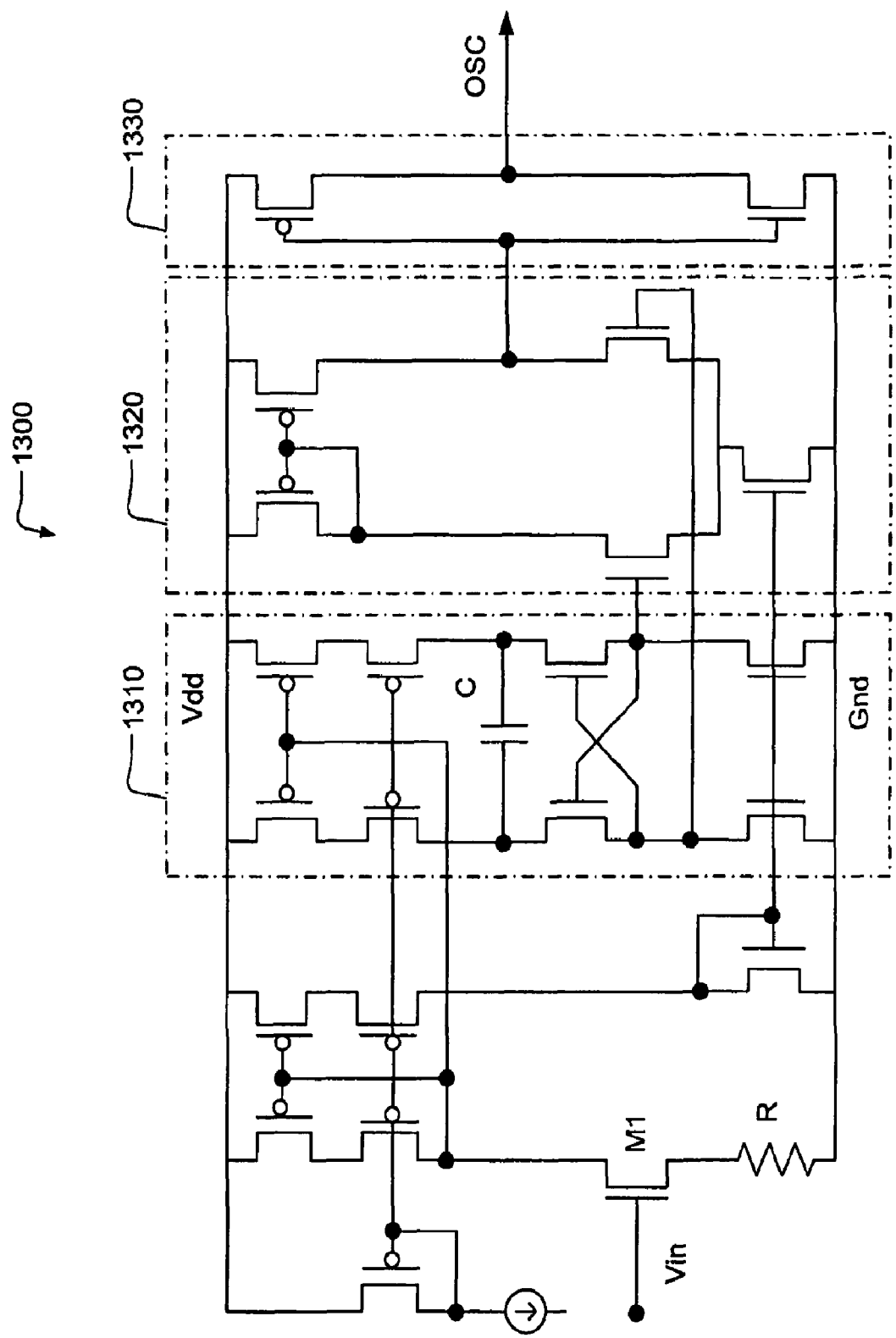
FIG. 14 shows one embodiment of a schematic diagram of a low power voltage control oscillator.
Figure 15:
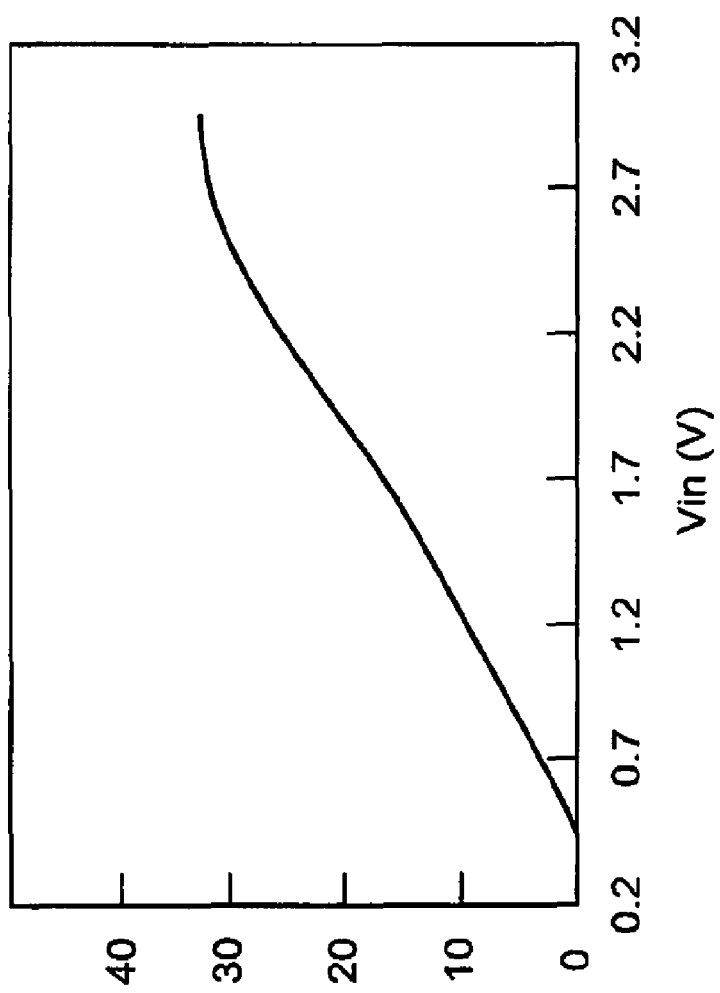
FIG. 15 shows the simulation results for the low power voltage control oscillator of FIG. 14.

FIG. 14 shows one embodiment of a schematic diagram of a low power voltage control oscillator ("VCO") 1300. The VCO 1300 significantly reduces the VCO current consumption from 650 μA to 100 μA. The low power VCO 1300 contains a source capacitive coupled VCO 1310, a differential to single end conversion circuit 1320, and an output buffer 1330. The simulation result for this circuit is shown in FIG. 15. The VCO 1200 has a tuning range from several hundred kHz to 50 MHz, and a gain of 20 MHz/V. It should be understood that other embodiments are available.

Figure 16:
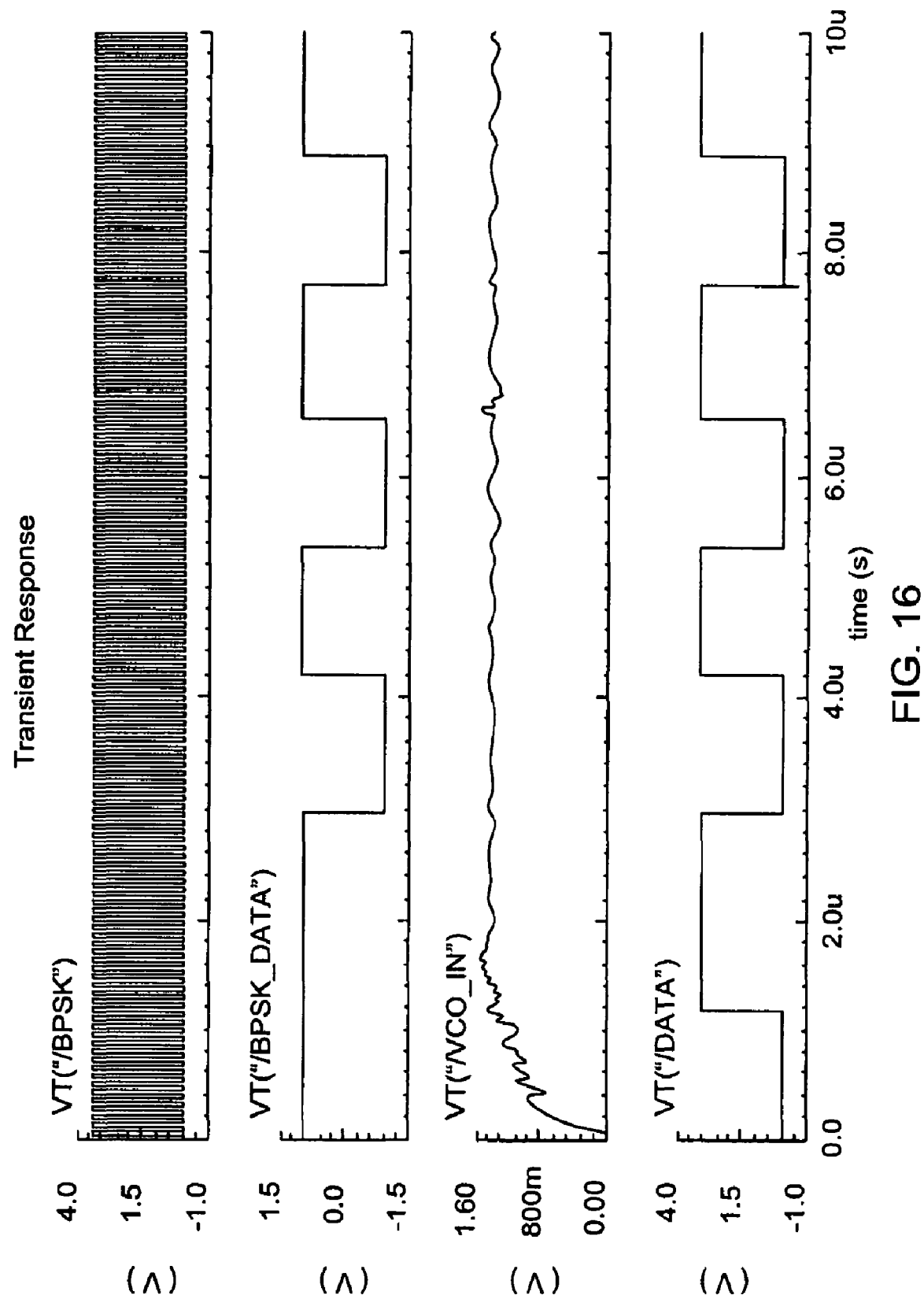
FIG. 16 shows the simulation results for the BPSK demodulator of FIG. 12.

The performance of the BPSK Modulator 1100 (FIG. 12) is overviewed in Table II and is illustrated in FIG. 16.

TABLE II

| SIMULATION PARAMETER VALUES | | | |
|---|---|---|---|
| Icp | 70 μA | $\Phi_p$ | 45° |
| $K_{VCO}$ | 14M · 2π rad/s · V | $C_1$ | 10 pF |
| $f_{carrier}$ | 13.56 MHz | $C_2$ | 50 pF |
| BR | 847.5 kBit/s | $R_2$ | 7.7 kΩ |
| $\xi$ | 0.854 | $\omega_p$ | 1M · 2π rad/s |

"BPSK" and "BPSK_DATA" are the input BPSK signal and BPSK data signal respectively. "VCO_IN" is the VCO control voltage, and "DATA" is the demodulated BPSK data signal. The BPSK data rate is 847.5 kBit/s (13.56 MHz/16). The counter 1154 provides a hold time of about 0.59 μs by counting 8 carrier clock signals. The current consumption of the whole chip is less than 600 μA.

The following documents are herein incorporated by reference in their entirety:
1. A. Harb, Y. Hu, and M. Sawan, "Low-power CMOS interface for recording and processing very low amplitude signals," J. Analog Integrated Circuits Signal Process., vol. 39, pp. 39-54, 2004;
2. Roland E. Best, "Phase-Locked Loops—Design, Simulation, and Applications", 5th Edition, McGraw-Hill;
3. Jeff Feigin, "Practical Costas loop design—Designing a simple and inexpensive BPSK Costas loop carrier recovery circuit." RF signal processing, www.rfdesign.com;
4. Yamu Hu, Mohamad Sawan, "A fully integrated low-power BPSK demodulator for implantable medical devices", IEEE Transections on Circuits and System, Vol. 52, No. 12, December 2005;
5. R. Jacob Baker, Harry W. Li, David E. Boyce, "CMOS Circuit Design, Layout, and Simulation", Wiley-IEEE Press;
6. Dean Banerjee, "PLL Performance, Simulation, and Design, Fourth Edition";
7. William F. Egan, "Phase-Lock Basics", A Wiley-Interscience Publication;
8. National Semiconductor Application Note 1001, "Analysis and Performance of Passive Filter Design of Charge Pump PLL's";
9. Behzad Razavi, "Design of Analog CMOS Integrated Circuits", McGraw-Hill Higher Education;
10. M. Ghovanloo, K. Najafi. "A Modular 32-site wireless neural stimulation microsystem", IEEE J. Solid-State Circuits, vol. 39, no 12, pp. 2457-2466, December 2004;
11. Ghovanloo, M.; Najafi, K. "A wideband frequency-shift keying wireless link for inductively powered biomedical implants". IEEE Transactions on Circuits and Systems I, Volume 51, Issue 12, December 2004;
12. Liu, W.; Vichienchom, K.; Clements, M.; DeMarco, S. C.; Hughes, C.; McGucken, E.; Humayun, M. S.; De Juan, E.; Weiland, J. D.; Greenberg, R. "A neuro-stimulus chip with telemetry unit for retinal prosthetic device;" Solid-State Circuits, IEEE Journal of Volume 35, Issue 10, October 2000 Page(s): 1487-1497;
13. Cahn, C. "Improving Frequency Acquisition of a Costas Loop", Communications, IEEE Transactions on [legacy, pre-1988], Volume 25, Issue 12, December 1977 Page(s): 1453-1459; and
14. Peric, M.; Manojlovic, P.; Peric, D.; "Improving Costas loop pull in range using pseudo BER detector" Telecommunications in Modern Satellite, Cable and Broadcasting Service, 2001. TELSIKS 2001. 5th International Conference on, Volume 2, 19-21 September 2001 Page(s): 753-756 vol. 2.

The above-described systems and methods can be implemented in digital electronic circuitry, in computer hardware, firmware, and/or software. The implementation can be as a computer program product (i.e., a computer program tangibly embodied in an information carrier). The implementation can, for example, be in a machine-readable storage device, for execution by, or to control the operation of, data processing apparatus. The implementation can, for example, be a programmable processor, a computer, and/or multiple computers.

A computer program can be written in any form of programming language, including compiled and/or interpreted languages, and the computer program can be deployed in any form, including as a stand-alone program or as a subroutine, element, and/or other unit suitable for use in a computing environment. A computer program can be deployed to be executed on one computer or on multiple computers at one site.

Method steps can be performed by one or more programmable processors executing a computer program to perform functions of the invention by operating on input data and generating output. Method steps can also be performed by and an apparatus can be implemented as special purpose logic circuitry. The circuitry can, for example, be a FPGA (field programmable gate array) and/or an ASIC (application specific integrated circuit). Modules, subroutines, and software agents can refer to portions of the computer program, the processor, the special circuitry, software, and/or hardware that implements that functionality.

Processors suitable for the execution of a computer program include, by way of example, both general and special purpose microprocessors, and any one or more processors of any kind of digital computer. Generally, a processor receives instructions and data from a read-only memory or a random access memory or both. The essential elements of a computer are a processor for executing instructions and one or more memory devices for storing instructions and data. Generally, a computer can include, can be operatively coupled to receive data from and/or transfer data to one or more mass storage devices for storing data (e.g., magnetic, magneto-optical disks, or optical disks).

Comprise, include, and/or plural forms of each are open ended and include the listed parts and can include additional parts that are not listed. And/or is open ended and includes one or more of the listed parts and combinations of the listed parts.

While this invention has been particularly shown and described with references to preferred embodiments thereof, it will be understood by those skilled in the art that various changes in form and details may be made therein without departing from the scope of the invention encompassed by the appended claims.

What is claimed is:

1. A low power BPSK demodulator, comprising:
a first branch having a first mixer and a first low pass filter;
a second branch coupled to the first branch and having a second mixer, wherein coupling between the first and second branches allows signal communication between the first and second branches; and
a third branch coupled to the second branch and having a second low pass filter and a voltage control oscillator, wherein coupling between the third and second branches allows signal communication between the third and second branches, and wherein the third branch and the second branch form a charge pumped based phase lock loop that locks onto a carrier frequency of the BPSK demodulator.

2. The BPSK demodulator of claim 1, wherein the third branch further includes a phase frequency detector and a charge pump.

3. The BPSK demodulator of claim 1, wherein the first branch includes a trigger and hold circuit for extracting data transition information from a phase lock loop fluctuation.

4. The BPSK demodulator of claim 3, wherein the trigger and hold circuit comprising:
a trigger circuit;
a transistor coupled to the trigger circuit;

a capacitor coupled to the transistor;
a resistor coupled to the capacitor; and
a D-Latch coupled to the resistor.

5. The BPSK demodulator of claim 4, wherein the transistor is a MOSFET type transistor.

6. The BPSK demodulator of claim 3, wherein BPSK data signal/information is extracted from the trigger and hold circuit.

7. The BPSK demodulator of claim 3, wherein the trigger and hold circuit comprising:
a counter;
an RS-latch coupled to the counter;
an AND gate coupled to the RS-latch;
a D-latch coupled to the AND gate; and
a glitch generator coupled to the AND gate.

8. The BPSK demodulator of claim 7, wherein at each BPSK data transition, the RS-latch is triggered disabling the D-latch and enabling the counter to start counting a CARRIER signal.

9. The BPSK demodulator of claim 8, wherein the D-latch is enabled and the counter is disabled when the count of the CARRIER signal equals eight.

10. The BPSK demodulator of claim 1, wherein the voltage control oscillator is a low power voltage control oscillator.

11. A low power BPSK demodulator, comprising:
a means for mixing a BPSK signal and a carrier signal to form a mixed signal;
a means for filtering the mixed signal to form a data signal;
a means for mixing the data signal and the carrier signal to form a regenerated BPSK signal;
a means for filtering the regenerated BPSK signal to form a filtered signal; and
a means for controlling the oscillation of the filtered signal to form the carrier signal.

12. A method of low power BPSK demodulation, comprising:
mixing, by a first mixer, a BPSK signal and a carrier signal to form a mixed signal;
filtering, by a first low pass filter, the mixed signal to form a data signal;
mixing, by a second mixer, the data signal and the carrier signal to form a regenerated BPSK signal;
filtering, by a second low pass filter, the regenerated BPSK signal to form a filtered signal; and
controlling, by a voltage control oscillator, the oscillation of the filtered signal to form the carrier signal.

* * * * *